US010753905B2

(12) United States Patent
Leite et al.

(10) Patent No.: US 10,753,905 B2
(45) Date of Patent: Aug. 25, 2020

(54) ISOTOPICALLY-LABELED PROTEOME STANDARDS

(71) Applicant: LIFE TECHNOLOGIES CORPORATION, Carlsbad, CA (US)

(72) Inventors: John Leite, Vista, CA (US); Robert Pope, Coralville, IA (US); Mahbod Hajivandi, Carlsbad, CA (US); Xiquan Liang, Escondido, CA (US)

(73) Assignee: Life Technologies Corporation

( * ) Notice: Subject to any disclaimer, the term of this patent is extended or adjusted under 35 U.S.C. 154(b) by 192 days.

(21) Appl. No.: 15/597,928

(22) Filed: May 17, 2017

(65) Prior Publication Data

US 2017/0254775 A1  Sep. 7, 2017

Related U.S. Application Data

(60) Division of application No. 13/951,354, filed on Jul. 25, 2013, now Pat. No. 9,733,213, which is a continuation of application No. 13/092,593, filed on Apr. 22, 2011, now abandoned, which is a division of application No. 11/368,996, filed on Mar. 7, 2006, now Pat. No. 7,939,331.

(60) Provisional application No. 60/659,635, filed on Mar. 7, 2005.

(51) Int. Cl.
*G01N 27/62* (2006.01)
*G01N 33/60* (2006.01)
*G01N 33/68* (2006.01)

(52) U.S. Cl.
CPC ............. *G01N 27/62* (2013.01); *G01N 33/60* (2013.01); *G01N 33/6848* (2013.01); *G01N 33/6851* (2013.01); *G01N 2458/15* (2013.01); *Y10T 436/24* (2015.01)

(58) Field of Classification Search
None
See application file for complete search history.

(56) References Cited

U.S. PATENT DOCUMENTS

| | | | |
|---|---|---|---|
| 3,591,768 A | 7/1971 | Torres | |
| 4,950,608 A | 8/1990 | Kishimoto et al. | |
| 5,229,580 A | 7/1993 | Chioniere | |
| 5,665,539 A | 9/1997 | Sano et al. | |
| 5,985,548 A | 11/1999 | Collier et al. | |
| 5,990,456 A | 11/1999 | Kilbride et al. | |
| 6,117,631 A | 9/2000 | Nilson | |
| 6,197,599 B1 | 3/2001 | Chin et al. | |
| 6,391,649 B1 | 5/2002 | Chait | |
| 6,511,809 B2 | 1/2003 | Baez et al. | |
| 6,642,059 B2 | 11/2003 | Chait | |
| 6,670,194 B1 | 12/2003 | Aebersold et al. | |
| 6,818,454 B2 | 11/2004 | Goshe et al. | |
| 7,396,688 B2 | 7/2008 | Estell et al. | |
| 7,939,331 B2 | 5/2011 | Leite et al. | |
| 8,940,546 B2 | 1/2015 | Grothe, Jr. et al. | |
| 9,252,003 B2 | 2/2016 | Hermanson et al. | |
| 2003/0157720 A1 | 8/2003 | Li | |
| 2004/0033530 A1 | 2/2004 | Awrey et al. | |
| 2004/0072251 A1 | 4/2004 | Anderson | |
| 2004/0229283 A1 | 11/2004 | Gygi et al. | |
| 2007/0031911 A1 | 2/2007 | Leite et al. | |
| 2016/0154006 A1 | 6/2016 | Hermanson et al. | |

FOREIGN PATENT DOCUMENTS

| | | |
|---|---|---|
| CH | 279883 | 12/1951 |
| JP | 7052977 | 6/1995 |
| WO | WO-1998/030684 | 7/1998 |
| WO | WO-0067017 A1 | 11/2000 |
| WO | WO-02071066 A1 | 9/2002 |
| WO | WO-03078962 A2 | 9/2003 |
| WO | WO-2004031730 A2 | 4/2004 |
| WO | WO-2011116028 A1 | 9/2011 |
| WO | WO-2012170549 A1 | 12/2012 |
| WO | WO-2014066117 A2 | 5/2014 |
| WO | WO-2014127144 A2 | 8/2014 |
| WO | WO-2014184320 A1 | 11/2014 |

OTHER PUBLICATIONS

Lee et al.,"A novel method for selective isotope labeling of bacterially expressed proteins", Journal of Biomolecular NMR, 5: 93-96 (1995). (Year: 1995).*
Blagoev, B. et al., "Temporal Analysis of Phosphotyrosine-Dependent Signaling Networks by Quantitative Proteomics", *Nature Biotechnology*, vol. 22(9), Aug. 15, 2004, 1139-1145.
Bonk, T. et al., "MALDI-TOF-MS Analysis of Protein and DNA", *Neuroscientist*, vol. 7, No. 1, 2001, 6-12.
Conrads, T. et al., "Quantitative analys if Bacterial and Mammalian proteomes using a combination of cysteine affinity tags and 15-N-netabikuc kabekubg", *Analytical Chem.*, 73(9), 2001, 2132-2139.
Ekins, R. et al., "Microarrays: their origins and applications", *Trends in Biotechnology*, vol. 17(6), Jun. 1, 1999, 217-218.
Everley, P. et al., "Quantitative cancer Proteomics : Stable isotope labeling with amino acids in cell culture (SILAC) as a tool for prostate cancer research", *Molecular & Cellular Proteomics*, vol. 3(7), 2004, 729-735.

(Continued)

*Primary Examiner* — Anand U Desai

(57) ABSTRACT

The invention provides methods for quantifying biomolecules, such as polypeptides in mass spectrometric analysis. The methods include use of a biomolecule standard having at least one atomic isotope different than that of the naturally occurring isotopes in the biomolecule of interest. Methods of the present invention also include methods for quantifying biomolecules where the copy biomolecule standard is made by expressing the biomolecule using a recombinant cell. Further included are the biomolecule standards themselves, method for making such standards, kits, systems, reagents, and engineered cells relating to the use of biomolecule standards in mass spectrometric analysis.

10 Claims, 3 Drawing Sheets

(56) References Cited

OTHER PUBLICATIONS

Foster, L. et al., "Unbiased Quantitative Proteomics of Lipid Rafts Reveals High Specificity for Signaling Factors", *Proceedings of the National Academy of Sciences (PNAS)*, vol. 100, No. 10, May 13, 2003, 5813-5818.
Ibarrola, N. et al., "A Proteomic Approach for Quantitation of Phosphorylation Using Stable Isotope Labeling in Cell Culture", *Anal. Chem.*, vol. 75, No. 22, Nov. 15, 2003, 6043-6049.
Karas, J. et al., "Matrix Assisted Ultrviolet Laser Desorption of Non-volatile Compounds", *Mass Spectrom. Ion Processes*, vol. 78, Sep. 24, 1987, 53.
Oda, Y. et al., "Accurate Quantitation of Protein Expression and Site-Specific Phosphorylation.", *Proceedings of the National Academy of Sciences (PNAS)*, vol. 96, No. 12, Jun. 1999, 6591-6596.
Ong, S. et al., "Mass spectrometric-based approachedin quantitative proteomies", *Methods*, vol. 29(2), Feb. 2003, 124-130.
Ong, S. et al., "Stable Isotope Labeling by Amino Acids in Cell Culture, SILAC as a Simple and Accurate Approach to Expression Proteomics", *Molecular & Cellular Proteomics*, 1(5), May 2002, 376-386.
PCTUS2006008058, , "International Preliminary Report on Patentability", dated Mar. 3, 2009.
PCTUS2006008058, , "International Search Report", dated Jul. 25, 2008.
PCTUS2006008058, , "Written Opinion", dated Jul. 25, 2008.
Walter, G. et al., "Protein arrays for gene expression and molecular interaction screening", *Current Opinion in Microbiology*, vol. 3, No. 3, Jun. 1, 2000, 298-302.
Wu, C. et al., "Metabolic Labeling of Mammalian Organisms with Stable Isotopes for Quantitative Proteomic Analysis", *Analytical Chemistry*, vol. 76(17), Sep. 1, 2004, 4951-4959.
Zor, T. et al., "Linearization of the Bradford Protein Assay increases its sensitivity: Theoretical and experimental studies", *Analytical Biochemistry*, vol. 236, No. 2, 1996, 302-308.
Bystrom, et al., "Plasma Renin Activity by LC-MS/MS: Development of a Prototypical Clinical Assay Reveals a Subpopulation of Human Plasma Samples with Substantial Peptidase Activity," Clinical Chemistry, 2010, 56(10): 1561-1569.
Desiderio, "Mass Spectrometric Analysis of Neuropeptidergic Systems in the Human Pituitary and Cerebrospinal Fluid," Journal of Chromatography B, 1999, 731:3-22.
Extended European Search Report dated Mar. 23, 2017, from corresponding European Patent Application No. 14806982.6, 16 pages.
Farzan et al.,"Sulfated Tyrosines Contribute to the Formation of the C5a Docking Site of the Human C5a Anaphylatoxin Receptor", J. Exp. Med. 193(9): 1059-1065 (2001).
Jager et al.,"Chapter 2: Radiolabeled amino acids: basic aspects and clinical applications in oncology", The Journal of Nuclear Medicine , pp. 23-58 (2001).
Partial European Search Report dated Dec. 2, 2016, from corresponding European Patent Application No. 14806982.6, (corresponding to PCT/US2014/041208), 7 pages.
Wang et al., "Screening Combinatorial Libraries by Mass Spectrometry. 2. Identification of Optimal Substrates of Protein Tyrosine Phosphatase SHP-1", Biochemistry 41: 6202-6210 (2002).

\* cited by examiner

ISOTOPICALLY-LABELED PROTEOME STANDARDS

CROSS-REFERENCE TO RELATED APPLICATIONS

This patent application is a divisional application of U.S. Non Provisional application Ser. No. 13/951,354, filed Jul. 25, 2013, which is a continuation application of U.S. Non Provisional application Ser. No. 13/092,593, which was filed Apr. 22, 2011, with is a divisional application of U.S. Non Provisional application Ser. No. 11/368,996 filed Mar. 7, 2006, which claims the benefit of priority of U.S. Provisional Patent Application No. 60/659,635 filed on 7 Mar. 2005, entitled "Isotopically-Labeled Proteome Standards." The content and subject matter of this patent application are hereby incorporated by reference in their entireties, including all text and figures.

FIELD OF THE INVENTION

The present invention relates generally to the field of mass spectrometry analysis of biomolecules, and more specifically to mass spectrometry analysis of proteins. The present invention provides isotopically-labeled biomolecule standards, such as protein standards, that may be used in mass spectrometry methods of quantifying a biomolecule in a sample. The present invention further provides methods of making such biomolecule standards, reagents, and kits.

BACKGROUND

Mass spectrometry (MS) is a powerful analytical technique that is used to identify unknown compounds, to relatively quantify known compounds, and to elucidate the structure and chemical properties of molecules.

Traditionally, proteome analysis has been performed using a combination of high resolution gel electrophoresis, in particular, two-dimensional (2D) gel electrophoresis, to separate proteins, and mass spectrometry to identify proteins. Typically, separation is by isoelectric focusing, which separates proteins by charge in a pH gradient, followed by SDS-PAGE, which separates proteins by molecular weight. After staining and separation, the mixture appears as a two-dimensional array of spots of separated proteins. Spots are excised from the gel, enzymatically digested, and subjected to mass spectrometry for identification. Relative quantitation of the identified proteins can be performed by observing the relative intensities of the spots via image analysis of the stained gel. However, because ionization efficiency of different protein fragments varies greatly, comparative quantification using mass spectrometry is unreliable.

Alternatively, peptides have been labeled isotopically before gel separation and expression levels quantified by mass spectrometry or radiographic methods. Absolute concentrations have not been achievable using these methods.

2D gels have a number of drawbacks. In particular, the approach is sequential and tedious, and is additionally fundamentally limited in that many biologically important classes of proteins, such as nuclear proteins or membrane proteins, are practically undetectable using these methods. Very acidic or basic proteins, very large or small proteins, and membrane proteins are either excluded or underrepresented in 2D gel patterns. Low abundance proteins, including regulatory proteins, are rarely detected when entire cell lysates are analyzed, reflecting a limited dynamic range. These deficiencies are detrimental for quantitative proteomics.

Protein standards for 2D gels are generally known. 2D gels separate proteins and polypeptides based on size. For example, US Patent application 20030157720 discloses a protein standard set that is based upon commercial protein standards providing polypeptides as standards for calculating molecular weight and the amount of peptide present.

However, in mass spectrometry, separation is not based on size alone, but separation is based on a mass to charge ratio. The mass to charge ratio is accurately obtained by MS. However, MS fragments are not easily assigned to a particular protein without sequencing (which is possible with many popular MS machines). Different peptides have different ionization efficiencies and patterns for MS, which prevents accurate comparison of one protein or polypeptide to another as is seen with 2D gels. An ideal MS standard should behave identically to the protein being measured during preparation for MS as well as within the MS.

Because it can provide detailed structural information, mass spectrometry is currently a valued analytical tool for biochemical mixture analysis and protein identification. For example, capillary liquid chromatography combined with electrospray ionization tandem mass spectrometry has been used for large-scale protein identification without gel electrophoresis. Qualitative differences between spectra can be identified, and proteins corresponding to peaks occurring in only some of the spectra are considered as candidate biological markers. Mass spectrometry analyses are not quantitative, however. In most cases, quantitation in mass spectrometry requires an internal standard, a compound introduced into a sample at known concentration. Spectral peaks corresponding to sample components are compared with the internal standard peak height or area for quantitation. Ideally an internal standard has elution and ionization characteristics similar to and preferably identical to those of the target compound but preferably the standard generates ions with a detectably different mass-to-charge ratio.

Using internal standards for complex biological mixtures is problematic. In many cases, the compounds of interest are unknown a priori, preventing appropriate internal standards from being devised. The problem is more difficult when there are many compounds of interest. In addition, biological samples are often available in very low volumes, and addition of an internal standard can dilute mixture components significantly. Low-abundance components, often the most relevant or significant ones, may be diluted to below noise levels and hence undetectable. Also, it can be difficult to judge the proper amount of internal standard to use. Thus internal standards are not widespread solutions to the problem of protein quantitation.

To reliably identify a biomolecule, such as a protein, from a sample, mass spectrometry (MS) based methods for proteomics rely on identification of a fragment ion, for example a peptide generated by the sequence specific fragmentation of a protein. Therefore, biomolecules, such as proteins and carbohydrates generally need to be enzymatically or chemically fragmented prior to mass spectrometric analysis. A protein generally generates a large number of peptides and hence a large number of peptides must be sequenced for each experiment.

Stable isotope labeling with amino acids in cell culture (SILAC) was developed as a useful tool for assaying relative concentrations of proteins of cells grown in culture. SILAC incorporates a label into proteins for mass spectrometric (MS)-based proteomics. SILAC relies on metabolic incorporation of a "light" or "heavy" form of an amino acid into proteins.

In a SILAC experiment, two groups of cells are grown in culture media that are essentially identical except in one respect: one media contains a "light" and the other a "heavy" form of a particular amino acid (for e.g. L-leucine or deuterated L-leucine). Thus, conventional SILAC techniques rely on growing parallel cultures where one set of cultures is grown in media containing an isotopically-labeled amino acid (such as $^{15}$N-Arg) and the other culture set is grown in conventional media thereby allowing an investigator to challenge one set of cultures with an external stimulus to monitor the relative changes in expression. With each cell doubling the cell population replaces at least half of the original form of the amino acid, eventually incorporating 100% of a given "light" or heavy form of the amino acid. Thus, when the labeled analog of an amino acid is supplied to cells in culture instead of the natural amino acid, it is incorporated into all newly synthesized proteins. After a number of cell divisions, each instance of this particular amino acid will be replaced by its isotope-labeled analog. Because there little chemical difference between the labeled amino acid and the natural amino acid isotopes, the cells behave like the control cell population grown in the presence of normal amino acid.

Conventional SILAC processes two culture lysates that are mixed and proteolyzed with optionally one or more stages of affinity enrichment. Unlabeled and labeled samples can be combined prior to lysis of the cells and treated as a single sample in all subsequent steps. This allows the experimenter to use any method of protein or even peptide purification (after enzymatic digestion) without introducing error into the final quantitative analysis.

SILAC methods are disclosed for example, in U.S. Pat. No. 6,391,649 to Chait. In SILAC, quantitation by mass spectrometry (MS) is performed by measuring the relative peak intensities of the heavy-labeled and the light-labeled isoforms of the peptides. Unlike chemical labeling techniques (e.g. isotopically coded affinity tagging (ICAT) or iTRAQ, Applied Biosystems, Framingham Mass.), the incorporation of isotopically heavy amino acid is nearly 100%. The difference in the mass of the isotope in each cell pool results in two distinct, closely spaced peaks for each protein or peptide actively produced by the samples in the mass spectrum. One peak corresponds to a protein or peptide from a protein from the cell pool with the normal abundance of isotopes. The other peak corresponds to a protein or peptide from the cell pool enriched in one or more of the isotopes. A ratio is computed between the peak intensities of at least one pair of peaks in the mass spectrum. The relative abundance of the protein in each sample may be determined based on the computed ratio. The protein may be identified by the mass-to-charge ratios of the peaks in the mass spectrum, as well as by other means known in the art.

Up to the point of the MS, none of the steps of the Chait process discriminates between a protein that contains the natural abundance of isotopes from the same protein from the enriched sample. Thus, the ratios of the original amounts of proteins from the two samples are maintained, normalizing for differences between extraction and separation of the proteins in the samples.

With labeled cells in SILAC, one can proceed to do sub-cellular purification of intact organelle structures or multi-protein complexes. The two samples can be combined as whole cells and a single subcellular preparation of nuclei, mitochondria, etc., then prepares the samples (now combined) for MS. Any sample preparation bias introduced by the comparison of two separate preparation steps (as would be the case in a chemical modification method) is avoided. SILAC is thus proven as a useful tool for proteomic analysis.

An example of a typical SILAC experiment is illustrated in FIG. 1. FIG. 1 depicts two identical cultures grown in parallel where one culture is grown under media conditions that enrich the $^{15}$N isotope of an amino acid (such as arginine) and the other is grown in conventional media. One of the cultures is challenged by an external stimulus (such as application of a drug). After the stimulus, the cell cultures are processed and lysates are produced. The lysates from each culture are mixed and proteolyzed with an enzyme such as trypsin. After some chromatography, the sample is analyzed by MS. MS analysis is capable of resolving the sample components by mass and measuring the relative abundance of the light and heavy isoforms of a specific peptide. The light and heavy isoforms will appear as two peaks differing in mass by the difference in mass due to the heavy isotope present. Proteins unaffected by the challenge will have a like ratio of the heavy isoform to light isoform peaks. A different ratio of the heavy isoform to light isoform indicates which culture (challenged or control) has increased or decreased expression of that protein.

Despite the advantages of SILAC over conventional chemical labeling techniques for quantifying expressed proteins, there are several limitations of the technique. As the name of the technique implies, incorporation of the heavy isotope requires protein expression in active cell cultures. Thus, the technique cannot be applied to tissue samples, biopsies or tissue slices. Another limitation is that protein quantitation by SILAC is merely relative (i.e. the relative expression of a specific protein in one experimental condition versus another) in like treated parallel samples. SILAC does not provide quantitation information to allow comparison of concentration of different molecules, for example different proteins. Absolute concentration information is not obtained using SILAC. Further, because SILAC does not provide absolute quantitation, a comparison of results between experiments is difficult to analyze.

Accordingly, MS and SILAC are useful tools. However, MS analysis does not lend to easy absolute quantitation, but only relative quantitation of the molecules analyzed. SILAC suffers from its ability to only provide information of relative concentration comparing protein concentration between samples, and absolute quantity information may not be obtained using SILAC.

SUMMARY OF THE INVENTION

The present invention provides mass spectrometry methods of quantifying a biomolecule in a sample, which utilize isotopically-labeled biomolecule standards. The present invention further provides isotopically-labeled biomolecule standards, such as protein standards and methods of making the same. According to certain embodiments, the biomolecule standards of the present invention are prepared using recombinant methods. The present invention further provides reagents and kits relating to the methods and products disclosed herein.

These and other features and aspects of the present invention are further described below. The descriptions provided are meant to describe the present invention with example embodiments. The example embodiments are not considered as limiting the scope of the claimed invention.

BRIEF DESCRIPTION OF THE DRAWINGS

The invention is herein described, by way of example, with reference to the following accompanying drawings.

DETAILED DESCRIPTION OF THE INVENTION

Figure 1:
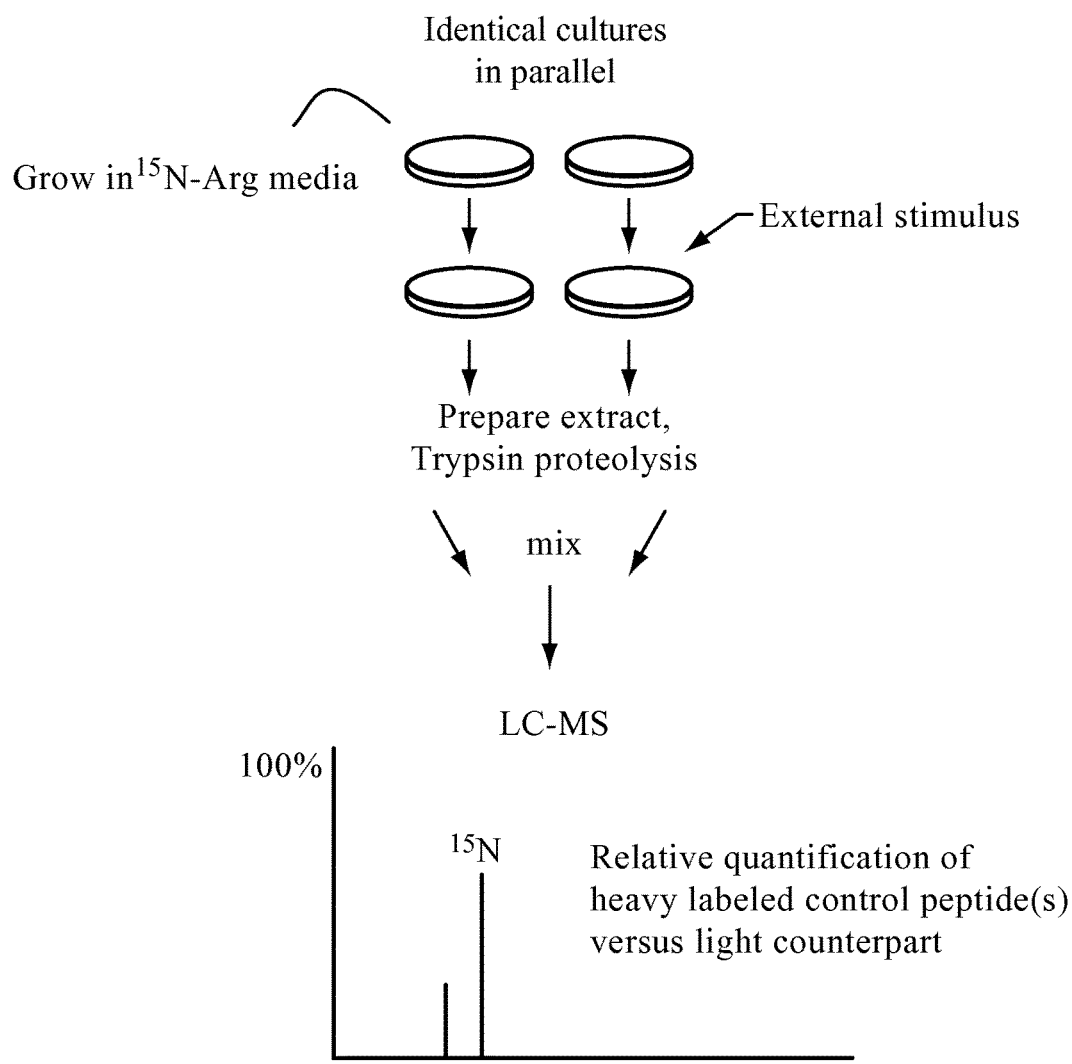
FIG. 1 is a diagram illustrating a conventional SILAC procedure.

The aspects, advantages and other features of the invention will become apparent in view of the following detailed description, which discloses various non-limiting embodiments of the invention. The following descriptions are by way of illustration and not by way of limitation.

The art would be aided by tools and methods for absolute quantitation of mass spectrometry samples, especially biomolecules subjected to MS analysis. Furthermore, the art would be aided by tools and methods allowing comparison of samples other than those obtained from cell culture, for example, samples from tissues, biopsies, serum, etc. The present invention provides such tools and methods.

The present invention provides isotopically-labeled biomolecule standards, which may be useful in quantification of one or more biomolecules, such as proteins. Isotope-labeled biomolecule standards of the present invention may be controllably manufactured or expressed. Thus, the biomolecules are produced in culture or by other means separately, and then added to one or more cell lysates as a set of internal quantitation standards for MS analysis. Embodiments utilizing recombinant expression result in reduced volumes of heavy isotope necessary for each experiment; and allow a single standard production run to be used over time for multiple samples (thus greatly reducing the cost of the experiment).

Embodiments utilizing recombinant expression can also be used to synthesize isotopically-labeled macromolecules (for example, nucleic acid molecules, protein molecules, polysaccharides) that can be used directly in MS, such as MALDI-TOF MS, to quantitate macromolecules. Large biomolecules (for example, biomolecules greater than S kDa, greater than 10 kDa, or greater than 20 kDa) can also be fragmented, using enzymes such as, but not limited to, proteases (including for example serine proteases, sulfhydryl proteases, metalloproteases), phosphorylases, peptidases, diesterases, lipases, oxidoreductases, transferases, hydrolases, lyases, or isomerases. The fragments can be used to quantitate the biomolecule of interest or to determine relative and absolute amounts of variants of macromolecules (such as variants having different polymer lengths, biochemical modifications, etc.).

Recombinant techniques that use engineered cells or cell extracts programmed with a recombinant nucleic acid template can be used to synthesize biomolecule standards by introducing a gene that encodes a biomolecule of interest into a cell (or cell extract) or by introducing a gene that encodes an enzyme or regulator that controls the synthesis of the copy biomolecule in a cell or cell extract. These methods can result in the synthesis of macromolecules, such as, but not limited to, proteins, nucleic acid molecules, and polysaccharides, that can be isotopically labeled during synthesis, purified, quantitated, and subsequently fragmented to obtain a set of biomolecule standards that comprise copy isotopically-labeled fragments of the biomolecule of interest such that MS of a sample that includes a fragmented biomolecule of interest includes multiple copy fragment standards that can be used to quantitate biomolecule variants in the sample. For example, splice variants of proteins or nucleic acid molecules and enzymatically modified biomolecules (including, but not limited to, proteolytically processed proteins, post-translationally modified proteins, polyadenylated RNAs, etc.) can not only be detected, but quantitated by use of a set of fragment standards generated from a macromolecule.

The present invention is advantageous over prior methods for example, in enabling accurate quantitation of biomolecules analyzed by MS by spiking a copy biomolecule standard, i.e., a biomolecule that reacts preferably biologically and chemically like the biomolecule copied, into a sample. The copy molecule is differentiable under MS from the biomolecule copied, for example by the incorporation therein of an isotopic label. Thus, knowing the quantity and/or concentration of the copied biomolecule introduced into the MS process allows an accurate determination of the relative or absolute quantity of the biomolecule copied. Alternatively, relative changes could be analyzed if the same amount (e.g., volume) of the biomolecule copy is added to two samples and relative peak intensities are analyzed. Comparison of concentrations of a peptide of interest in two samples may be enabled, with or without determining an absolute concentration of the copy molecule.

The present invention can be used for quantitation of one or more polypeptides in a sample. The methods include adding an isotopically-labeled copy polypeptide of interest of known quantity to a sample that contains the polypeptide of interest (or a variant thereof, for example, a splice variant, a polypeptide generated from a different member of a gene family, a variant having one or more post-translational modifications); analyzing the sample by mass spectrometry; and comparing the mass spectrometry peaks of pairs resulting from the isotopically-labeled copy polypeptide of interest and the polypeptide of interest of the sample, in which the isotopically-labeled copy polypeptide differs from the mass of the polypeptide of interest by an amount corresponding to the difference in mass between the labeling isotope and the cognate naturally-occurring isotope, taking into account the number of labeled isotopes incorporated into the polypeptide. The methods further include comparing peak heights of the members of a peak pair to quantitate the polypeptide of interest in the sample, taking into account the known mass of the added copy polypeptide.

In some embodiments, the polypeptide copy and the polypeptides of the sample are fragmented prior to MS. In these embodiments, fragment peaks are compared and used to quantitate the amount of individual fragments of a polypeptide of interest. In some aspects, multiple fragments of a copy polypeptide can thus be used to assess the internal consistency of the quantitation for a given polypeptide of interest. In other aspects, multiple fragments of a copy polypeptide can be used to determine the relative and absolute abundance of splice variants or differentially modified variants of a protein of the sample. In these aspects, for example, at least one fragment generated from the copy polypeptide prior to MS is preferably within or substantially overlaps a protein domain that is encoded by an alternatively spliced exon of a gene encoding the polypeptide of interest, or is within or substantially overlaps a domain of the protein that can be proteolytically processed in a cell, or includes a post-translational modification site.

In other embodiments, copy and sample polypeptides may not be fragmented prior to MS. In these embodiments, polypeptide standards are synthesized in engineered cells or in in vitro protein synthesis systems. The polypeptide standards and sample polypeptides can be analyzed, for example, by MALDI-TOF MS to quantitate the amount of protein in a sample.

The present invention is also advantageous in that it allows researchers to extend advantages of the SILAC technique (such as making use of the efficiency of heavy isotope labeling and its steadfastness with respect to changes to protein conformation, compartmentalization or aggregation state that might alter the accessibility of reaction sites, etc.) to samples involving non-cultured cells, for example, tissue samples, including blood, serum, semen, sputum, cerebrospinal fluid (CSF), saliva, etc, tissue slices, biopsies, aspirates, necropsies, etc. Another advantage of the present invention is the accurate quantitation of proteins that are not actively transcribed/translated, since the sample itself does not have to incorporate label for quantitation of proteins. Cells that do not divide in culture, for example, neural cells, can also be used for quantitation of biomolecules such as proteins. Quantitation is also possible for cells that are not cultured—for example, cells of an organism, embryos, tissues, organs, or bodily fluids. The present invention allows absolute quantitation of proteins in addition to relative quantitation of proteins.

The present invention is also advantageous over prior methods, such as SILAC, in that it further enables use in culture as well as in tissue slices and even samples obtained from living organisms.

In describing embodiments of the present invention, specific terminology is employed for the sake of clarity. However, the invention is not intended to be limited to this specific terminology. It is to be understood that each specific element includes all technical equivalents that operate in a similar manner to accomplish a similar purpose. Additionally, elements and features of the embodiments described can be combined with other embodiments of the invention to create new embodiments that are also included in the present invention. Further, all of the citations herein are incorporated by reference in their entirety.

Unless defined otherwise, all technical and scientific terms used herein have the same meaning as commonly understood by one of ordinary skill in the art to which this invention belongs. Generally, the nomenclature used herein are well known and commonly employed in the art. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

As used herein, "a", "an" and "the" may mean one or more. As used herein, "another" may mean at least a second or more.

As used herein, an "analytical result" of mass spectrometry is typically expressed as a peak or collection of peaks that indicate mass of a particle. However a peak is only one mode of indicating relation of mass to charge. "Peak" is used to indicate a distinct particle separated based on its mass/charge ratio regardless of the mode through which the data are expressed.

As used herein, the term "biomolecule" is intended to include any biomolecules for which quantification may be desired, including, but not limited to whole proteins, glycoproteins, lipoproteins, and other polypeptides; carbohydrates; peptides; nucleic acids, lipids, glycolytic fragments; sugar compounds; polysaccharides and the like.

A "copy" of a biomolecule may be for example, a biomolecule, such as a polypeptide that behaves in a chemical and electrostatic fashion that is essentially identical to the polypeptide copied. The copy may be longer or shorter than the copied polypeptide and/or may differ in sequence in some regions from the copied polypeptide. However, at least one fragment of the copy, for example, a tryptic fragment, will behave ionicly and chemically as a fragment of the same region of the polypeptide copied. By way of non-limiting example, arginines synthesized with a heavy nitrogen isotope will have essentially the same biological and chemical properties as natural arginine. When this heavy arginine is incorporated into a polypeptide, the arginine residue will behave the essentially the same whether it is natural or a copy; the protein will similarly behave the same whether containing a heavy or light isotope. Cleavage at this residue, for example, by a tryptic enzyme, will produce a peptide fragment of heavier mass due to the terminal high mass arginine, but with the same chemical and ionizing characteristics as the peptide fragment from a natural peptide. For example, the tryptic enzyme may be trypsin or an enzyme with cleavage characteristics similar to trypsin, such as TRYPle™ (Invitrogen, Carlsbad, Calif.). The high mass polypeptide from which the high mass peptide is cleaved is thus for the purposes of the present invention considered a copy of the natural polypeptide, although flanking regions of the copy peptide fragment may or may not have the same characteristics as flanking regions of the natural polypeptide. For example, as discussed further below, the copy may include a tag or marker to facilitate or monitor synthesis and/or to aid purification.

A "derivative" of a cell or cell line is a cell or cell population whose lineage can be traced to a specific cell or cell line, such as a specific passage of the cell or cell line. An engineered cell generally will not be considered a derivative if a chromosome altered by engineering contains a marker or lacks a marker not found or found, respectively, in the chromosome or region of the cell or cell line whose source of derivation is questioned.

As used herein, an "engineered cell" is a cell that has an unnatural genome, that is, a cell whose genetic material has been altered by man. The altered genome may include an episome (such as a plasmid), or a viral construct (such as an adenoviral construct, adeno-associated viral construct, and alphaviral construct, a retroviral construct, etc.), that is introduced into the cell, or a deletion of, addition to, or mutation of a genome of an organelle, or one or more chromosomes of the cell. Genetic engineering can also comprise one or more of homologous recombination, expression or introduction of antisense RNA, expression or introduction of RNAi, inappropriate expression of a gene, or expression of a dominant negative form of a gene.

As used herein, an "expression product" takes on a meaning broader than the product of transcription and translation. An expression product can also be a product that results from a reaction within a cell that is guided by a gene, for example, a transgene.

As used herein, the terms "heavy-isotope labeled biomolecule," and "isotopically-labeled biomolecule" mean a biomolecule that has incorporated in its chemical structure, an isotope of an atom that is different from the predominant isotope found in nature. In context, an atom refers to a plurality of atoms having the same atomic number.

In various aspects, the invention includes mass spectrometry. As used herein, the term "mass spectrometry" (or simply "MS") encompasses any spectrometric technique or process in which molecules are ionized and separated and/or analyzed based on their respective molecular weights. Thus, as used herein, the terms "mass spectrometry" and "MS" encompass any type of ionization method, including without limitation electrospray ionization (ESI), atmospheric-pressure chemical ionization (APCI) and other forms of atmospheric pressure ionization (API), and laser irradiation. Mass spectrometers are commonly combined with separation methods such as gas chromatography (GC) and liquid chromatography (LC). GC or LC separates the components in a mixture, and the components are then individually introduced into the mass spectrometer; such techniques are generally called GC/MS and LC/MS, respectively. MS/MS is an analogous technique where the first-stage separation device is another mass spectrometer. In LC/MS/MS, the separation methods comprise liquid chromatography and MS. Any combination (e.g., GC/MS/MS, GC/LC/MS, GC/LC/MS/MS, etc.) of methods can be used to practice the invention. In such combinations, "MS" can refer to any form of mass spectrometry; by way of non-limiting example, "LC/MS" encompasses LC/ESI MS and LC/MALDI-TOF MS. Thus, as used herein, the terms "mass spectrometry" and "MS" include without limitation APCI MS; ESI MS; GC MS; MALDI-TOF MS; LC/MS combinations; LC/MS/MS combinations; MS/MS combinations; etc.

"Means for synthesizing" a polypeptide, biomolecule, protein, and the like, simply refers to tools that might be used for peptide synthesis, for example, a gene, host cell, in vitro translation system (such as Invitrogen Expressway™ Translation Systems), a buffer, a medium, amino acids, amino acid precursors, a solid phase synthesis system, or component part thereof.

As used herein, a "polypeptide" is a polymer of amino acids linked by peptide bonds. As used herein, a "protein" is a polypeptide, that is, a polymer of amino acids. The terms "protein" and "polypeptide" are used somewhat interchangeably herein. While the protein may have biologic activity, no inference of a requirement for activity is to be made. A protein may contain modifications to the amino acid monomers. For example, a protein may be glycosylated or phosphorylated. "Protein" includes protein containing molecules such as lipoproteins and glycoproteins. The terms "polypeptide" and "peptide" are used somewhat interchangeably herein. In the art, "peptide" is simply a molecule containing peptide bonds. The term "peptide" is generally used to describe fragments of a protein or polypeptide, for example, resulting from enzymatic or chemical digestion, for example, using a tryptic enzyme or cyanogens bromide. But the term "polypeptide" may similarly include fragments thereof. In analysis by mass spectrometry, a polypeptide is often split into multiple peptides, for example, two, three, four, five, six, seven or more peptide components from the polypeptide. Analysis of any one of these peptide fragments yields information with respect to the source polypeptide. When data from plural peptides are confirmatory, confidence in the analysis is increased. Terms such as "polypeptide of interest", "protein of interest" and "biomolecule of interest" include any source polypeptide, protein or biomolecule or peptide bond containing fragment thereof about which an investigator seeks information.

A "substantially non-radioactive isotope" is an isotope or mixture of isotopes whose disposal is not regulated by rules designed to protect the public from radiation exposure.

A "synthesized copy" is a copy made by any non-natural means, that is, a copy made as a result of the intervention of man. For example, synthesis may be accomplished by providing chemicals and reaction conditions in sequence to produce a desired biomolecule; by providing an in vitro translation system, such as a cell extract in vitro transcription/translation system; by providing a host cell (prokaryotic or eukaryotic) and a template for the host cell to use for manufacturing a biomolecule of interest such as a polypeptide; or by providing chemicals and/or catalysts, such as enzymes, to produce a desired biomolecule. The synthetic process may include a concentration process, a purification process, an enriching process, etc. including photoreactive processes to facilitate use of the synthesized copy in a desired process or analysis.

The terms "quantitation" and "quantification" and forms thereof, are used interchangeably herein.

A "transgene" as used herein, is a nonnatural gene or a gene that has been translocated to a nonnatural location or environment.

Methods of Quantifying One or More Biomolecules

The present invention includes methods for quantifying one or more biomolecules, such as proteins or other polypeptides in a sample using mass spectrometry. Such methods may include providing at least one sample having a biomolecule of interest to be quantified; providing a copy of the biomolecule of interest, in which the copy is made using an isotope having a mass different than that of naturally-occurring isotopes of the biomolecule of interest; quantifying the biomolecule of interest in the copy; introducing a known quantity of the copy into said sample; analyzing the sample by mass spectrometry; and comparing obtained mass spectrometry peak pairs resulting from the one or more biomolecule or a fragment thereof, and the copy or a fragment thereof to determine the quantity of the mass spectrometry peak pairs differ in mass by an amount corresponding to the isotope with the different mass taking into account the number of isotope atoms in each ion monitored.

Other embodiments of the present invention include methods for quantifying one or more biomolecules using a biomolecule standard made using recombinant expression. Such methods may include for example, providing at least one sample having a biomolecule of interest to be quantified; providing a copy of the biomolecule of interest, in which the copy is made using recombinant expression and the copy includes an isotope having a mass different than that of naturally occurring isotopes of the biomolecule of interest; quantifying the biomolecule of interest in the copy; introducing a known quantity of the copy into the sample; analyzing the sample by mass spectrometry; and comparing obtained mass spectrometry peak pairs resulting from the one or more biomolecules or one or more fragments thereof, and the copy or one or more fragments thereof to determine the quantity of the one or more biomolecules in the one or more samples.

Samples in accordance with the present invention may include for example, at least one component selected from the group consisting of biological cells, a cell supernatant, a cell extract, embryos, a cell lysate, viruses, biological tissue, a tissue slice, an organ, an organism, a collection of organisms, a portion of an organism, a biopsy, a sample of bodily fluid, a blood sample, a serum sample, and a cell-free biological mimetic system.

The copy of the biomolecule of interest is labeled with at least one isotope to form a standard. Non-limiting examples of isotopes for labeling include $^2H$, $^{13}C$, $^{15}N$, $^{17}O$, $^{18}O$, $^{34}S$, etc. Preferably the isotope is a heavy isotope that is substantially non-radioactive isotope. By isotope-labeled biomolecule, is meant a biomolecule that has incorporated in its chemical structure an isotope of an atom that is different from the predominant isotope found in nature. Thus, the label is a mass-altering label. The mass of the label should be such that upon MS analysis, a peak associated with the biomolecule is distinguishable from a peak associated with the isotope-labeled biomolecule.

The biomolecule standard may be chemically synthesized or may take advantage of biological processes or molecules. The labeled atom or molecule is incorporated into the biomolecule and spiked into a sample for quantitation of one or more biomolecules in the sample.

According to certain embodiments, the copy of the biomolecule (e.g., polypeptide or protein) of interest may be made by example, using free cell synthesis or an engineered cell. Engineered cells of the present invention may be cells derived from a cell or cell line other than a cell or cell line from which the sample is obtained.

According to certain embodiments, the biomolecule standard may be made using recombinant methods, such as in vitro translation and synthesis in an engineered cell or a cultured cell. For example, copies of the biomolecule may be made by expressing the biomolecule from an engineered construct in a cultured cell (which can be episomal or incorporated into a host cell chromosome), or from a cell that has been engineered (genetically modified) to overexpress or inducibly express an endogenous gene or a gene recombined into the cell's genome (recombinant cells). Generation of the reference standard for quantitative analysis of expressed proteins by recombinant methods has a number of advantages over using a control cell culture. One advantage is the reduced amount and cost of isotopically-labeled amino acid. Another advantage is the ability to efficiently synthesize isotopically-labeled macromolecules. Methods for making biomolecule standards using recombinant methods are described further below.

The copy of the polypeptide includes at least one isotope in an amino acid or amino acid residue of the polypeptide. According to certain embodiments, the polypeptide includes at least one substantially nonradioactive isotope. Isotopes used in accordance with the present invention have a mass different than that of naturally occurring isotopes of the polypeptide of interest, and may include for example, at least one isotope selected from the group consisting of $^{15}$N, $^{13}$C, $^{18}$O, $^{2}$H and $^{34}$S. Amino acids having mass-altering isotopes can be any amino acids, including naturally-occurring amino acids, modified amino acids, and synthetic amino acids that can be incorporated into peptides and proteins, and are preferably naturally-occurring amino acids. Non-limiting examples of the amino acids or amino acid residues useful for making isotopically-labeled polypeptide copies include those selected from the group consisting of Arg, Lys, Asp, Glu, Met, Trp, Ser, Thr, Tyr, and Asn.

According to certain embodiments, the copy may be made using an isotope pool. For example, the labeling isotope may be present in a pool of molecules containing the labeling isotope as a predominant fraction of the pool. The isotope pool may include for example, substantially non-radioactive isotopes. By way of non-limiting example, the isotope pool may include at least one isotope having a mass distribution different than that of naturally occurring isotopes in the polypeptide of interest. For example, the labeling isotope may be present in a pool of molecules, such as a pool of amino acids including one or more of, for example, arginine, threonine, serine, tyrosine molecules in a fraction for example at least about 100%, 99%, 98%, 95%, 90%, 80%, 75% of the pool. Higher fractions are expected to provide higher quality data.

Certain embodiments for example, use amino acids labeled with $^{15}$N or $^{13}$C, more preferably $^{15}$N-Arg or $^{13}$C-Arg. This expression will be used as an exemplary shorthand expression for the heavy-isotope labeled biomolecules of the present invention. For example, a pool of $^{15}$N-Arg would include a significant, i.e., measurable, difference from a natural pool of Arg. The pool of atoms, e.g. a pool where $^{15}$N predominates may be incorporated into a biomolecule. Labeled biomolecules synthesized using the pool will be distinguishable, for example in MS from natural forms of the biomolecule.

A biomolecule standard may be quantified, for example, by biochemical or spectroscopic methods as known in the art for the particular type of biomolecule. The biomolecule standard may then be used for example, as a quantitative internal reference for a sample cell lysate. A protein standard can be quantified by protein quantitation assays as they are known in the art, for example, ELISA, Bradford assays, Lowry assays, bicinchoninic acid (BCA) assays, or modified versions of these, or fluorescence based assays, such as are commercially available (for example, Quant iT™ Assay Kit [Invitrogen], NanoOrange® Protein Quantitation kit [Invitrogen], EZQ™ Protein Quantitation kit [Invitrogen], FluoroProfile™ [Sigma-Aldrich]).

The biomolecule standard may then be introduced into the sample to be analyzed. According to certain embodiments, the quantitation standard is introduced into the sample as early in the processing of the sample as possible. This ensures that losses or modifications induced by the fractionation process occur evenly across the sample components and the reference standard(s).

Mass spectrometry provides a rapid and sensitive technique for the characterization of a wide variety of molecules. In the analysis of peptides and proteins, mass spectrometry can provide detailed information regarding, for example, the molecular mass (also referred to as "molecular weight" or "MW") of the original molecule, the molecular masses of peptides generated by proteolytic digestion of the original molecule, the molecular masses of fragments generated during the ionization of the original molecule, and even peptide sequence information for the original molecule and fragments thereof.

A time-of-flight mass spectrometer determines the molecular mass of chemical compounds by separating the corresponding molecular ions according to their mass-to-charge ratio (the "m/z value"). Ions are accelerated in the presence of an electrical field, and the time necessary for each ionic species to reach a detector is determined by the spectrometer. The "time-of-flight" values obtained from such determinations are inversely proportional to the square root of the m/z value of the ion. Molecular masses are subsequently determined using the m/z values once the nature of the charged species has been elucidated.

A particular type of MS technique, matrix-assisted laser desorption time-of-flight mass spectrometry (MALDI-TOF MS) (Karas et al., Int. J. Mass Spectrom. Ion Processes 78:53, 1987), has received prominence in analysis of biological polymers for its desirable characteristics, such as relative ease of sample preparation, predominance of singly charged ions in mass spectra, sensitivity and high speed. MALDI-TOF MS is a technique in which a UV-light absorbing matrix and a molecule of interest (analyte) are mixed and co-precipitated, thus forming analyte:matrix crystals. The crystals are irradiated by a nanosecond laser pulse. Most of the laser energy is absorbed by the matrix, which prevents unwanted fragmentation of the biomolecule. Nevertheless, matrix molecules transfer their energy to analyte molecules, causing them to vaporize and ionize. The ionized molecules are accelerated in an electric field and enter the flight tube. During their flight in this tube, different molecules are separated according to their mass to charge (m/z) ratio and reach the detector at different times. Each molecule yields a distinct signal. The method is used for detection and characterization of biomolecules, such as proteins, peptides, oligosaccharides and oligonucleotides, with molecular masses between about 400 and about 500,000 Da, or higher. MALDI-MS is a sensitive technique that allows the detection of low ($10^{-15}$ to $10^{-18}$ mole) quantities of analyte in a sample.

Partial amino acid sequences of proteins can be determined by enzymatic or chemical proteolysis followed by MS analysis of the product peptides. These amino acid sequences can be used for in silico examination of DNA and/or protein sequence databases. Matched amino acid sequences can indicate proteins, domains and/or motifs having a known function and/or tertiary structure. For example, amino acid sequences from an uncharacterized protein might match the sequence or structure of a domain or motif that binds a ligand. As another example, the amino acid sequences identified by MS analysis can be used as antigens to generate antibodies to the protein and other related proteins from other biological source material (e.g., from a different tissue or organ, or from another species). There are many additional uses for MS, particularly MALDI-TOF MS, in the fields of genomics, proteomics and drug discovery. For a general review of the use of MALDI-TOF MS in proteomics and genomics, see Bonk et al. (*Neuroscientist* 7:12, 2001).

Tryptic peptides labeled with light or heavy amino acids can be directly analyzed using MALDI-TOF. However, where sample complexity is apparent, on-line or off-line LC-MS/MS or two-dimensional LC-MS/MS may be necessary to separate the peptides.

MS may be capable of resolving the heavy and light isotope isoforms for each peptide, as well as measuring the relative intensity of each isoform.

After MS is performed, mass spectrometry peak pairs result from each biomolecule being analyzed and its corresponding biomolecule standard having a different molecular weight. The mass spectrometry peak pairs may be compared to determine either an absolute or relative quantity of the one or more biomolecules in the sample. According to certain embodiments, the present invention features use of the protein standard to quantify proteins that share regions of sequence identity (such as homologous proteins or splice variants).

Methods of the present invention may further include forming fragments of the biomolecule, for example, by digestion with an enzyme or cleavage with a chemical reagent. Enzymes in accordance with the present invention may include for example, at least one enzyme selected from the group consisting of a protease (for example, a serine protease), a phosphorylase, a peptidase, a diesterase, a lipase and an oxidoreductase, a transferase, a hydrolase, a lyase, an isomerase, and a ligase.

According to certain embodiments, the at least one sample includes a plurality of samples. At least a first sample of the plurality of samples may have been exposed to a different set of conditions than a second sample of the plurality of samples. Non-limiting examples of different sets of conditions may include for example, species or strain from which the sample is obtained, disease-state versus normal state of an organism from which the sample is obtained; one or more of: chemical exposure; genetic manipulation; feeding regimen; environmental difference; aging or developmental stage; or difference in exposure to one or more hormones, growth factors, or cytokines.

Genetic manipulation may include for example, performing gene engineering. Genetic engineering can include one or more of: homologous recombination (for gene knockout or replacement), expression or introduction of antisense RNA, expression or introduction of RNAi, inappropriate expression of a gene, or expression of a dominant negative form of a gene. Chemical exposure may include for example, at least one of exposure to a drug or metabolite thereof, exposure to a drug candidate or metabolite thereof, addition of growth factors, and addition of cytokines to alter the phenotype of the cell. Environmental difference may include for example, exposure to different temperature, UV light, $O_2$ pressure, etc., or the presence of at least one of a virus, a bacteria and a carcinogen.

Methods according to the present invention may include providing at least a second sample whose polypeptide of interest is desired to be quantified; introducing a known quantity of the copy into the second sample; analyzing by mass spectrometry the second sample to determine a quantity of polypeptides of interest or a fragment thereof in said second sample; and comparing the quantity of at least one polypeptides of interest or one or more fragments thereof of the sample to the second sample. According to certain embodiments, the second sample may be from a preparation different from the sample.

According to certain embodiments, biomolecules of interest, such as proteins of interest, may be quantified from a cell lysate. Cells may be grown in culture or obtained from a tissue sample from an organism, for example, the tissue sample may be a tissue slice or a biopsy, for example a needle biopsy. The sample may be obtained for example, from a blood sample. The cell lysate is prepared from a cell population. Lysis can be accomplished in any fashion, for example, by detergent disruption, sonication, osmotic shock, freezing, etc. Embodiments of the invention may include for example, quantifying proteins from a cell lysate that originated from cells that expressed proteins recombinantly or naturally in cell culture, as well as samples that originated from plasma, serum, CSF, urine, sputum, semen, lymph, or any biological fluid, tissue or other sample. According to other embodiments of the present invention, proteins may be quantified from a cell lysate that originated from cells that have been challenged by an external stimulus such as application of a drug, radiation, or a change in the environment, such as a feeding schedule, temperature change, light dark cycle, etc.

According to other embodiments of the present invention, biomolecules, such as proteins may be quantified from healthy samples and compared to proteins quantified from disease samples. Comparing protein expression patterns between normal and disease conditions may reveal proteins whose changes are important in the disease aid thus, identify proteins which aid diagnosis or whose modification may be of therapeutic value. In clinical research, changes in protein expression may be useful indicators of targets of treatments, efficacy of treatments or monitoring unknown side effects of treatments. In basic research, changes in protein expression may be useful indicators of responses of a cell to experimental manipulation. Methods of detecting protein expression profiles may also have important applications in, for example and without limitation, tissue typing, drug screening, forensic identification, and clinical diagnosis.

Certain embodiments of the invention are directed to drug or toxicology screening. For example, a sample from a culture, a tissue or an organism exposed to a drug, a drug metabolite, a drug candidate or a drug candidate metabolite, may be analyzed to test efficacy, toxic effect, alternate uses, etc.

Another aspect of the present invention features quantifying the abundance of a biomolecule that is a non-protein biological metabolic product (i.e. such as lipids, fatty acids, DNA, steroids, carbohydrates, and the like). In this example, a heavy-isotope labeled biological molecule may be synthesized and then spiked into a lysate for the purpose of measuring the relative abundance to the naturally-occurring light-isotope isoforms. The abundance of the naturally occurring light form can then be determined.

Another aspect of the present invention may allow monitoring effects of stimuli or conditions, such as feed regimens, growth factors, cytokines, temperatures, pH, etc., for effects such as phenotypic effects on a cell, organism, or tissue. For example, differentiation or dedifferentiation, for example of adult or stem cells, e.g., differentiated cells or stem cells, hematopoietic stem cells, neural stem cells, cardiac stem cells, etc, may be monitored for differentiation or dedifferentiation markers. Cells in this aspect as well as other aspects may be human or other animal, for example, mammal, insect or fish. Rodent cells such as rat or mouse may be used. Food producing organisms such as plant or meat producing animals are likewise suitable sources for sample material and/or cells. Corn, grain, wheat, rice, ovine, porcine, equine, etc. tissues may supply samples. Samples may be used for possible commercial development or for experimental convenience.

Certain embodiments of the present invention include using at least one manufactured protein, for example, a recombinantly expressed and heavy-isotope labeled reference protein and/or set of proteins. A single protein may be investigated. However, multiple proteins or polypeptides can be manufactured to contain a heavy isotope. Any or all of the manufactured proteins can be spiked into a sample. In standard practice the peptides will each be resolved during MS analysis so that if the mass/charge profile of peptides from a protein or polypeptide is known, the quantity of the protein spiked into the sample can be used to calculate the quantity of the corresponding peak from the sample, after dilutions from introduction of the reference standard are accounted for.

Yet another aspect of the present invention features quantifying the abundance of biological derivatives, for example, biomolecules acted on by an environmental substance, for example a toxic substance. A known derivative may be synthesized, and used to spike one or more samples. A derivative may incorporate component atoms of the environmental substance or may result from interaction of a cell with the environmental substance.

Another aspect of the present invention features aiding identification of "ion-pairs" using "High/Low" mass spectrometry analysis. In "High/Low" MS, the user programs the MS instrument to alternate the experimental conditions during electrospray ionization such that the voltage cycles between high voltage settings (which induce fragmentation randomly along the backbone of a peptide) and low voltage settings (which preserve the integrity of the peptide backbone). Thus, during the low voltage settings, the instrument is analyzing the parent ions, and in during high voltage conditions these parent ions are all being fragmented simultaneously. This MS technique allows a user to analyze peptides as they elute from a liquid chromatography separation with a very high duty cycle. Because the "High/Low" technique does not use traditional MS/MS methods where one stage of MS selects a precursor mass, and a second stage of MS analyzes fragment ions generated by a collision cell, computational algorithms are required to decipher the data being generated. The present invention could aid the identification of "ion-pairs" that are separated by a set mass difference imparted by the number of heavy isotopes. These "ion-pairs" can assist in differentiating low-abundance signals from the background.

Yet another aspect of the invention features a quantitation method for assaying the quantity of a sample prepared, for example for SILAC, using a heavy isotope. This aspect features a non-heavy isotope that will act as a copy of the heavy isotope-labeled SILAC sample. In this aspect, the standard will appear as a lower mass peak compared to the high mass isotope sample.

Methods of Making Isotopically-Labeled Biomolecule Standards

The present invention further includes methods of making isotopically-labeled biomolecule standards using molecular biotechnology techniques, such as recombinant expression. Such methods may include for example, methods of making isotopically-labeled biomolecule standards, such as protein standards.

According to certain embodiments, a copy of the biomolecule of interest may be made by synthesizing the biomolecule in engineered cells. In some embodiments, the engineered cells have been genetically manipulated to overexpress or inappropriately express one or more enzymes that the cell uses to synthesize the biomolecule and/or one or more regulators of the synthesis of the biomolecule. A gene that encodes a biosynthetic enzyme or regulator can be introduced into a host cell, for example, optionally under the control of a regulatable promoter. The cell, which can be prokaryotic or eukaryotic, can be cultured in media that contains isotope labels (for example, heavy isotope labels) that are present in precursor molecules such as, but not limited to, acetyl CoA, sugars (such as hexose and pentose sugars), cholesterol, amino acids, nucleobases, etc. The cultured host cells can then be induced to synthesize the isotope-labeled biomolecule of interest.

In other embodiments, the engineered cells can be engineered to include a gene encoding the biomolecule of interest, such as a nucleic acid molecule or protein. The introduced gene may include gene regulatory sequences directing expression of the gene. The cell, which can be prokaryotic or eukaryotic, can be cultured in media that contains isotope labels (for example, heavy isotope labels) that are present in precursor molecules such as, but not limited to, sugars (such as hexose and pentose sugars), amino acids, nucleobases, etc. The cultured host cells can then be induced to synthesize the isotope-labeled biomolecule of interest.

In some embodiments, the biomolecule of interest is a protein (polypeptide), and host cells are engineered to contain a nucleic acid construct encoding the polypeptide of interest. The host cells can be prokaryotic or eukaryotic. The cells can be bacterial cells, for example, *E. coli* cells, *Bacillus* spp. cells (e.g., *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells); yeast cells (e.g., *Saccharomyces cerevisiae* cells and *Pichia pastoris* cells); insect cells (e.g., *Drosophila* (e.g., *Drosophila melanogaster*), *Spodoptera* (e.g., *Spodoptera frugiperda* Sf9 and Sf21 cells) and *Trichoplusa* (e.g., High-Five cells); nematode cells (e.g., *C. elegans* cells); avian cells (for example, UMNSAH-DF1 cells, QT6 cells, QT-35 cells); amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells). According to certain embodiments, cells may be selected from yeast cells, mammalian cells, marsupial cells, avian cells, insect cells, fish cells, amphibian cells, reptile cells, and nematode cells. Photosynthetic bacteria can also be used for protein production, and include, but are not limited to, green non-sulfur bacteria (e.g., *Choroflexus* spp. (e.g., *C. aurantiacus*), *Chloronema* spp. (e.g., *C. gigateum*)), green sulfur bacteria (e.g., *Chlorobium* spp. (e.g., *C. limicola*), *Pelodictyon* spp. (e.g., *P. luteolum*), purple sulfur bacteria (e.g., *Chromatium* spp. (e.g., *C. okenii*)), and purple non-sulfur bacteria (e.g., *Rhodospirillum* spp. (e.g., *R. rubrum*), *Rhodobacter* spp. (e.g., *R. sphaeroides, R. capsulatus*), *Rhodomicrobium* spp. (e.g., *R. vanellii*)).

The recombinant biomolecule copy, such as a protein copy may, for example, usefully be prepared by expression of the biomolecule in host cells. After insertion of the nucleic acid molecule or vector into a host cell (i.e., transformation of the host cell), the recombinant proteins may then be produced by expression in the host cells, and subsequently purified. In many cases, it may be preferred to synthesize a polypeptide quantitation standard in a cell type that can post-translationally modify the polypeptide of interest in the same manner as the source of the sample. In some embodiments, in which the source of a sample to be analyzed by MS is mammalian cells or tissue, the host cells used for synthesizing the biomolecule copy are eukaryotic cells, and in some preferred embodiments the host cells are mammalian, avian, or insect cells.

In other embodiments, the proteins may be expressed as inclusion bodies in bacterial host cells as described, for example, in PCT International Publication No. WO98/30684. Following rupture of the cells, inclusion bodies may be separated from cellular debris using suitable separation techniques such as centrifugation. Proteins contained in the inclusion bodies are subsequently solubilized using a denaturing agent and may be, if attached as a fusion protein to an inclusion partner protein, treated with a cleavage agent to remove the partner protein. In some cases, the denatured protein may be renatured prior to further purification.

In some embodiments, the recombinant proteins may be expressed in cell-free system. Such systems may facilitate, for example, the incorporation of the isotope labels into the expressed proteins. In certain embodiments, proteins expressed in a cell-free system are labeled using heavy isotopes.

Bacterial systems provide convenience and high-yields but not all expressed proteins may be stably expressed in bacterial systems. In addition, some extracts of eukaryotic cells may have post-translational modification systems that can be desirable for producing copy polypeptides. Thus, an in-vitro eukaryotic or prokaryotic expression system may be used for some proteins. A gene fragment may be expressed in a system where the buffer and/or media is depleted of one or more specific amino acids so that a low abundant isotope such as a $^{15}$N-enriched amino acid may be introduced for incorporation into the expressed protein.

In some embodiments, the recombinant proteins of the instant invention may be expressed as part of a chimeric or multimeric protein. A recombinant chimeric protein comprises protein sequences derived from different source proteins. A recombinant multimeric protein can include multiple repeats of one or more protein sequences, or can comprise the sequence of an entire protein multimerized in tandem.

The present invention includes selecting the gene or encoding the sequence of the protein of interest. This sequence may be obtained, for example, from one of many sequence databases (i.e. SwissProt, NCBi, etc.). Genes may also be obtained from libraries or commercial banks. Primers may be designed that target to a specific region of the sequence that is unique so that only a single gene fragment is amplified. The primers can optionally include promoter sequences (for example, T7, T3, or SP6 promoter sequences for in vitro translation), restriction sites, recombination sites, or sequences encoding peptide tags. These primers may then be used to amplify a gene fragment from a cDNA library or other source (such as Open Reading Frame (ORF) library, if differentiation between splice variants is a requirement of the analysis).

The amplified gene may, for example, then be subconed into an expression vector where the gene is transcribed and translated recombinantly. Subcloning may be performed by any number of possible methods available in the art. The polymerase chosen for this amplification reaction will depend on the subcloning scheme. Several subcloning kits for PCR products are available commercially.

This transcription/translation or other synthesis may be performed in culture or using a cell-free in-vitro method where the buffers and/or media are depleted of the naturally occurring light-isotope amino acid, and enriched with a heavy-isotope labeled substrate, for example, a labeled amino acid, sugar, lipid, etc. whose metabolism is desired to be investigated.

The fused vector may be used to transform a cell, for example, a competent bacterial cell, a eukaryotic cell or introduced into a cell free in vitro translation preparation. Bacterial cells will not glycosylate, so it may be preferred to transform a cell, for example, a eukaryotic cell, capable of glycosylation or a eukaryotic cell preparation capable of glycosylation. Preferably, the glycosylation pattern will be similar to or identical to a glycosylation pattern of the protein in the cell type under investigation.

Cell extracts for in vitro protein synthesis systems can be prokaryotic or eukaryotic. The cells used for making an extract can be bacterial cells, for example, *E. coli* cells, *Bacillus* spp. cells (e.g., *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells); yeast cells (e.g., *Saccharomyces cerevisiae* cells and *Pichia pastoris* cells); insect cells (e.g., *Drosophila* (e.g., *Drosophila melanogaster*), *Spodoptera* (e.g., *Spodoptera frugiperda* Sf9 and Sf21 cells) and *Trichoplusa* (e.g., High-Five cells); nematode cells (e.g., *C. elegans* cells); avian cells (for example, UMNSAH-DF1 cells, QT6 cells, QT-35 cells); amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells). Photosynthetic bacteria can also be used for protein production, and include, but are not limited to, green non-sulfur bacteria (e.g., *Choroflexus* spp. (e.g., *C. aurantiacus*), *Chloronema* spp. (e.g., *C. gigateum*)), green sulfur bacteria (e.g., *Chlorobium* spp. (e.g., *C. limicola*), *Pelodictyon* spp. (e.g., *P. luteolum*), purple sulfur bacteria (e.g., *Chromatium* spp. (e.g., *C. okenii*)), and purple non-sulfur bacteria (e.g., *Rhodospirillum* spp. (e.g., *R. rubrum*), *Rhodobacter* spp. (e.g., *R. sphaeroides, R. capsulatus*), *Rhodomicrobium* spp. (e.g., *R. vanellii*)). Plant cell extracts, such as wheat germ extracts, can also be used.

In vitro protein synthesis systems are known in the an and commercially available (for example the Invitrogen Expressway™ in vitro translation systems). The in vitro protein synthesis systems can be programmed by RNA or DNA (in vitro transcription/translation systems). Synthesis of RNA from a DNA template is well known in the art and commercial kits are available. Such in vitro translation systems can include one or more isotopically-labeled amino acids for incorporation into proteins.

Vectors expressing the proteins used in the compositions of the present invention may be, for example, phage, plasmid, or phagemid vectors. Expression vectors useful in the present invention include chromosomal-, episomal- and virus-derived vectors, e.g., vectors derived from bacterial plasmids or bacteriophages, and vectors derived from combinations thereof, such as cosmids and phagemids. The DNA insert encoding a protein may be operatively linked to an appropriate promoter known to the skilled artisan.

Expression vectors of the present invention may include at least one selectable marker. Such markers may include for example, tetracycline or ampicillin resistance genes for culturing in *E. coli* and other bacteria.

The vector may have been designed such that a fusion protein including the protein of interest and an affinity tag will be generated upon translation. For bacterial expression, selection for bacteria that contain the vector may be achieved by growth in antibiotic media.

After the desired gene fragment is subcloned, the fragment may be expressed, for example in a host expression cell, e.g., in a bacterial expression system, a eukaryotic expression such as a yeast cell, or a higher cell. When a host cell is used, it may be for example, a cell of the same tissue, species, genus, order, family or class as the source of the sample. Posttranscriptional modifications such as alternative splicing or posttranslational modifications such as glycosylations, phosphorylations, etc. may thus be maintained between samples and standards. According to certain embodiments, the cell is derived from a cell or cell line different from that of the sample. Representative examples of host cells appropriate for the expression of the instant recombinant proteins include, but are not limited to, bacterial cells such as *E. coli, Streptomyces* spp., *Erwinia* spp., *Klebsiella* spp., *Salmonella typhimurium*, and *Caulobacter crescentus*. Preferred as a host cell is *E. coli*, and particularly preferred are *E. coli* strains BL21(DE3), BL21-Star™ (DE3), BL21-AI™, TOP10, LMG194, G1724, which are available commercially (Invitrogen Corp., Carlsbad, Calif.). Other *E. coli* strains that may be used may include DH10B c1 and STBL2. In some cases the strains further contain other plasmids, such as, for example, pLysS or pLysE, for reduction of basal expression of recombinant proteins or for other reasons. Other examples of appropriate host cells for use in the expression of the recombinant proteins of the invention include yeast cells, insect cells, and mammalian cells.

The expressed fusion protein may then be isolated, by any suitable method. Expressed proteins may be purified by any of a variety of protein purification techniques that are well known to one of ordinary skill in the art. For example, the fusion protein may be isolated and purified using metal-chelate chromatography, antibody affinity chromatography or other techniques known to those skilled in the art. Suitable techniques for purification may include, but are not limited to at least one of the following techniques: ammonium sulfate or ethanol precipitation, acetone precipitation, acid extraction, electrophoresis, isoelectric focusing ("IEF"), immunoadsorption, anion or cation exchange chromatography, phosphocellulose chromatography, hydrophobic interaction chromatography, affinity chromatography, immunoaffinity chromatography, size exclusion chromatography ("SEC"), liquid chromatography ("LC"), high performance LC ("HPLC"), fast protein LC ("FPLC"), hydroxylapatite chromatography, lectin chromatography, immobilized metal affinity chromatography ("IMAC"), metal chelation chromatography, and continuous flow electrophoresis ("CFE").

Inclusion of an affinity tag, such as one or more histidine tags, may allow quick and easy purification of the expressed protein by affinity capture, for example with a metal chelate resin. A tag is not necessary however. Any desired tag including an immune recognized tag may be used. Non-limiting examples of affinity tags that may be used in accordance with the present invention include for example, V5, FLAG purification tag, c-myc or a poly-His tag (e.g., HH, HHH, HHHHHH or any polymer or combination thereof), polyHistidine, hemagglutinin, GST, biotin, GFP, and polycysteine (for example, tetracysteine), etc. The tag may alter the mass of only one peptide, for example a C-terminal peptide. Other peptides will be essentially identical in sequence and chemistry to the native protein, but differ in mass due to the use of the non-naturally present isotope.

The copy protein or polypeptide may be fragmented to produce multiple fragments for MS. For example at least two, three, four, preferably at least four, five, six or seven and more preferably at least eight nine, ten or more peptide fragments may result. Peptide fragments can be formed by any fragmentation process, for example by biological (such as enzymatic, e.g., tryptic) processes or by chemical processes (e.g., chemical cleavage. Tryptic enzymes and cyanogen bromide are preferred fragmentation instruments. Although a quantity can be assayed using a single peptide fragment confidence increases as more data is available. For example, additional fragments increase confidence that the copy is behaving as the copied molecule in fragmentation and MS and allow for averaging to increase confidence in the absolute values obtained.

Once purified, the biomolecule standard may be quantified by biochemical or spectroscopic methods. The concentration of the biomolecule can be assayed by one of many different commercially available methods, e.g., a Lowry assay, or any method chosen by the user.

The resulting biomolecule is an isotopically-labeled biomolecule standard. The standard may then be used for example, as a quantitative internal reference for a sample cell lysate.

Isotopically-Labeled Biomolecule Standards

The present invention is also directed to isotopically-labeled biomolecule standards, such as protein standards produced using molecular biology techniques. Such techniques may include techniques disclosed herein, such as recombinant techniques, or other techniques known by those skilled in the art.

In some embodiments, an isotopically-labeled MS quantitation standard is made by expressing a gene encoding a polypeptide of interest in a cell-free protein synthesis system, in which one or more isotopically-labeled amino acids is present in the cell-free synthesis system. In some embodiments, an isotopically-labeled MS quantitation standard is made by expressing a gene encoding a polypeptide of interest in cultured cells, in which one or more isotopically-labeled amino acids is present in the cell culture media. In preferred embodiments, the copy polypeptide may be fragmented, such as by proteolysis with a protease or chemical reagent, prior to MS analysis, using the same protease or chemical reagent used to fragment polypeptides of the sample.

In Vitro Translation System

The present invention further provides in vitro translation systems, which may include a population of biomolecule standard precursor molecules comprising at least one atomic isotope that under mass spectrometry produces at least one peak distinguishing said biomolecule standards from otherwise identical biomolecules lacking said at least one atomic isotope; and systemic components sufficient for translation comprising a catalyst and biomolecule precursor molecules to effect translation of said biomolecule.

Kits

The present invention includes kits for performing the methods, kits for producing the products of the present invention, and/or kits that include one or more products of the present invention. Accordingly, kits of the present invention may include any components that may be of assistance in performing such methods or producing such products. By way of non-limiting example, kits in accordance with the present invention may include kits for quantifying a biomolecule by mass spectrometry or kits for producing isotopically-labeled biomolecule or protein standards.

Kits in accordance with the present invention may include means for or one or more components for synthesizing isotopically-labeled biomolecule (e.g., protein) standards, for example using recombinant expression. By way of non-limiting example, such kits may include one or more components for performing in vitro translation, such as an in vitro peptide synthesis system. In vitro peptide synthesis systems may include for example, an extract selected from the group consisting of a bacterial extract, a eukaryotic extract, a plant extract, a mammalian extract, and an insect cell or arthropod extract, and one or more isotopically-labeled amino acids.

In another example, kits can include media, and isotopically-labeled amino acids for production of standards in cell culture. Kits may also include host cells. Kits may further include a template instruction for synthesizing a biomolecule standard.

Kits according to on aspect of the present invention include at least one amino acid containing one or more atomic isotopes that are different from naturally occurring isotopes. Non-limiting examples of amino acids in accordance with the present invention include one or more amino acids selected from the group consisting of Arg, Lys, Asp, Glu, Met, Trp, Ser, Thr, Tyr, and Asn. Non-limiting examples of isotopes in accordance with the present invention include one or more isotopes selected from the group consisting of $^{15}N$, $^{13}C$, $^{18}O$, $^{2}H$ and $^{34}S$.

In addition to an isotopically-labeled amino acid, in one aspect kits of the present invention can include one or more of: a culture medium for in vitro culture; a template instruction for synthesizing a biomolecule standard; a cell lysis reagent; a resin for purifying a biomolecule standard; a protein quantitation reagent; an enzyme or chemical reagent capable of cleaving said biomolecule standard; a host cell; a vector; and a polymerase.

Media provided in a kit for growing cells can include one or more isotopically-labeled amino acids, or the one or more isotopically-labeled amino acids can be provided separately. Media for cell culture for producing MS quantitation standards can be depleted in one or more amino acids, such as one or more amino acids that is provided in the kit in isotopically-labeled form. The kit can also include a cell lysis reagent, such as a buffer or detergent solution and/or one or more enzymes.

In another aspect of kits of the invention, in addition to an isotopically-labeled amino acid, kits can include one or more of: an in vitro protein synthesis system; a template instruction for synthesizing a biomolecule standard; a cell lysis reagent; a resin for purifying a biomolecule standard; a protein quantitation reagent; an enzyme or chemical reagent capable of cleaving said biomolecule standard; a host cell; a vector, and a polymerase.

The in vitro protein synthesis system comprises a cell lysate, which can be a prokaryotic or eukaryotic cell lysate, as described herein. The extract can be, for example, a bacterial extract, a eukaryotic extract, a plant cell extract, a mammalian cell extract, or an insect cell extract. The kit can further include at least one buffer for in vitro protein synthesis. A buffer for translation can include one or more salts, buffering compounds, nucleotides, amino acids, enzymes, or energy sources. Preferably an in vitro synthesis buffer that includes amino acids is depleted in one or more naturally-occurring amino acids that is provided in isotopically-labeled form.

Kits for production of MS protein quantitation standards using in vitro protein synthesis or cell culture systems can further include a resin for purifying a biomolecule standard, such as a protein standard. The resin can be, for example, chromatography media for affinity purification, and can included, without limitation, an Ni-NTA agarose matrix, or a matrix that includes bound maltose, calmodulin, biotin, an antibody, protein A, or other affinity capture reagents. A protein quantitation reagent included in a kit can include, without limitation, a BCA reagent, a Lowry assay reagent, a Bradford assay reagent, an ELISA reagent, or a reagent for fluorometric detection and quantitation.

Kits in accordance with the present invention may include an enzyme or chemical preparation capable of cleaving a biomolecule standard. Enzymes in accordance with the present invention may be for example, trypsin, Endo-Lys-C, Endo-Glu-C, AspN protease, yeast peptidase, V-8 protease, pepsin, subtilisin, proteinase 1c, and tobacco etch virus protease, or TRYPle.™ Chemical preparation in accordance with the present invention may include for example, Cyanogen Bromide.

The kits can further include host cells for the production of polypeptide standards, as provided herein. The kits can further include a vector. A vector can be an expression vector that includes expression sequences for transcription and/or translation. The vector can include a tag sequence, such as but not limited to a sequence encoding a polyHistidine tag, a FLAG tag, a c-myc tag, a hemagglutinin tag, GST, biotin, GFP, polycysteine, and tetracysteine. The kit can further include a polymerase, such as but not limited to a high temperature polymerase for nucleic acid amplification reactions, such as Taq, Pfu, or Pfx polymerase.

In another aspect, kits in accordance with the present invention may include a population of biomolecule standard precursor molecules, which may include at least one atomic isotope that under mass spectrometry produces at least one peak distinguishing the biomolecule standards from otherwise identical biomolecules lacking said at least one atomic isotope. Such kits may further include for example, a catalyst.

According to another aspect of the invention, kits may include isotopically-labeled biomolecule standards. The biomolecule standards may include at least one atomic isotope that under mass spectrometry produces at least one peak distinguishing the biomolecule standard from otherwise identical biomolecules lacking the at least one atomic isotope.

Kits in accordance with the present invention may also include a device for quantifiable spiking or introducing a biomolecule standard to a lysate.

The kits can further optionally include a MALDI matrix, such as, for example sinnapinic acid or alpha-cyano-4-hydroxycinnamic acid (CHCA).

In some embodiments, kits of the invention may further comprise mass spectrometric probes.

Reagents

The invention further provides reagents useful for performing any of the methods described herein. In certain aspects, a reagent according to the invention includes an isotopically-labeled biomolecule standard. The standard may be a subsequence of a known biomolecule and can be used to identify the presence of and/or quantify the biomolecule in a sample, such as a cell lysate. In other aspects, a pair or more of reagents are provided, which may include at least two isotopically-labeled biomolecule standards. One or more of the biomolecule standards in reagents of the present invention may optionally be modified.

Engineered Cells

The present invention further includes an engineered cell, which includes a transgene; and an expression product of the transgene, the expression product comprising at least one substantially non-radioactive isotope that under mass spectrometry produces at least one peak distinguishing the expression product from natural components of the cell.

The following examples illustrate non-limiting embodiments of the invention. The examples set forth herein are meant to be illustrative and should not in any way serve to limit the scope of the claimed invention. As would be apparent to skilled artisans, various changes and modifications are possible and are contemplated within the scope of the invention described, and may be made by persons skilled in the art without departure from the spirit of the invention.

Example 1

Figure 2:
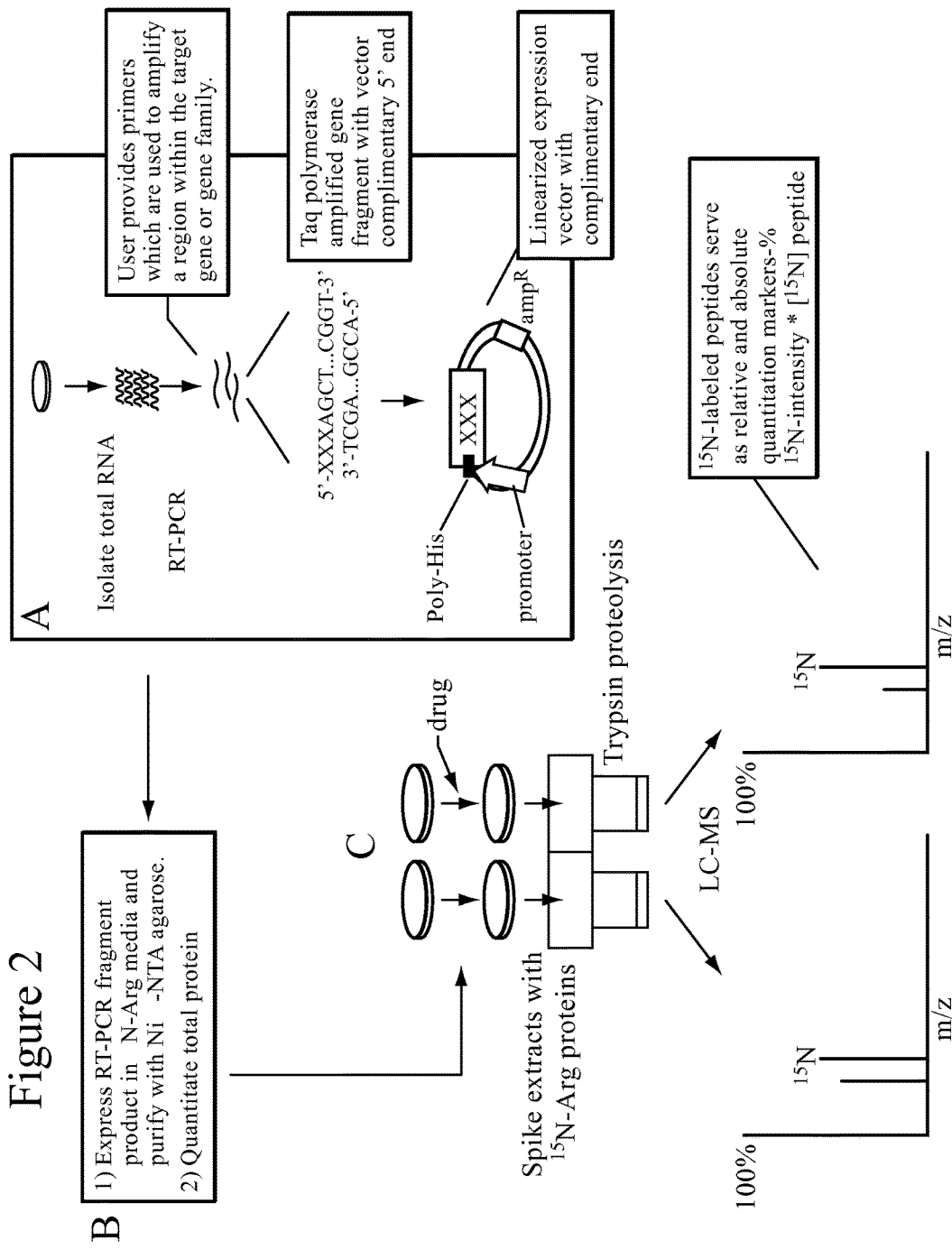
FIG. 2 illustrates a basic scheme according to certain embodiments of the present invention.

An example of a method of quantitation of a biomolecule in accordance with the present invention is shown in FIG. 2. According to these embodiments, the method includes selecting a biomolecule of interest, for example, a protein, or protein family, a lipid, a carbohydrate, or combination thereof. In FIG. 2, the biomolecule is a protein.

After the protein of interest is selected, a copy of the protein is made into a standard. Panel A describes the method for isolation of genes of interest and subcloning. According to the embodiments depicted in FIG. 2, the user selects a gene encoding the sequence of the protein of interest. Primers may be designed that target to a specific region of the sequence that is unique so that only a single gene fragment is amplified. These primers may then be used to amplify a gene fragment from a cDNA library.

The polymerase chosen for this amplification reaction will depend on the subcloning scheme. By way of non-limiting example, a polymerase that has terminase activity may be desired so that poly-adenosine tails are generated at the 3' end of the amplified gene fragment. These poly-adenosine tails are complimentary to the ends of a linearized expression vector with poly-thymidine 5' tails. A topoisomerase enzyme fuses the gene fragment to a vector. Alternatively, the primer design may include a complimentary sequence to an expression vector (as shown in FIG. 2, panel A).

After subcloning by any number of possible methods available in the art (several subcloning kits for PCR products are available commercially), the fused vector may then be used to transform a cell, for example, a competent bacterial cell, a eukaryotic cell or introduced into a cell free in vitro translation preparation. In vitro systems by their so nature produce fewer biomolecules than engineered cell systems as the in vitro systems do not synthesize all biomolecules that a living cell needs for maintenance. Bacterial cells will not glycosylate, so it may be preferred to transform a cell, for example, a eukaryotic cell, capable of glycosylation or a eukaryotic cell preparation capable of glycosylation. Preferably, in these embodiments the glycosylation pattern will be similar to or identical to a glycosylation pattern of the protein in the cell type under investigation. Also preferably the vector has been designed such that a fusion protein including the protein of interest and an affinity tag will be generated upon translation. For bacterial expression, selection for bacteria that contain the vector may be achieved by growth in antibiotic media (the vector confers resistance via a gene that is co-subcloned as illustrated by panel A of FIG. 2).

After the desired gene fragment is subcloned, the fragment may be expressed, for example in a host expression cell, e.g., in a bacterial expression system, a eukaryotic expression such as a yeast cell, or a higher cell; or in an in-vitro translation system.

Bacterial systems provide convenience and high-yields but not all expressed proteins may be stably expressed in bacterial systems. Thus, an in-vitro eukaryotic or prokaryotic expression system may be used for some proteins. A gene fragment may be expressed in a system where the buffer and/or media is depleted of one or more specific amino acids so that a low abundant isotope such as a $^{15}N$-enriched amino acid may be introduced for incorporation into the expressed protein. Inclusion of an affinity tag may allow quick and easy purification of the expressed protein by affinity capture, for example with a metal chelate resin.

Because the protein expressed will normally be fragmented, for example by enzymatic (e.g., tryptic) or chemical digestion, many peptides will result. The tag preferably will alter the mass of only one peptide, for example a C-terminal peptide. Other peptides will be essentially identical in sequence and chemistry to the native protein or polypeptide, but differ in mass due to the use of the non-naturally present isotope. According to the example depicted in FIG. 2, the product is purified using $Ni^{2+}$-NTA agarose. Upon purification, the concentration of protein can be assayed by one of many different commercially available methods, e.g., a Lowry assay, or any method chosen by the user. An embodiment of this process is shown in FIG. 2, panel B.

FIG. 2, part C illustrates an embodiment of the present invention where a plurality of pools of cells are analyzed in parallel (these pools may be comprised of cell cultures or a plurality of tissue samples). At least one set of cells may be exposed to an external stimulus or manipulation. Subsequently, lysates of the cell pools are generated. A known concentration of the protein standard isolated for example, according to the embodiments shown in panels A and B of FIG. 2, is spiked into each cell lysate.

Following proteolysis, the lysate components are processed for MS. For example, they may be separated by chromatography and fed to MS. In this example, the concentration of the light-isotope isoform is determined by comparing the relative intensity to its heavy-isotope isoform. Because the absolute concentration of the heavy-isotope isoform is known, the absolute concentration of the light-isotope isoform may be determined. One assumes that because the heavy and light isotope isoforms are chemically essentially identical, and because the heavy labeled isoform was spiked into the sample prior to any fractionation, that recovery of both isoforms from the fractionation is essentially identical.

In this example, to compare the expression of proteins in plurality of pools, for example, a control cell pool and an experimentally challenged cell pool, two MS analyses would be performed. Using the present invention, however, each run will not require a control sample because the absolute concentration can be determined. Multiple MS analyses are within the capability of normal operations, for example, operations of a MS core lab.

Example 2

According to this example, a protein standard is made as in Example 1. In this example, a known amount of the protein standard, although not quantified is added to at least two of the cell pools. Relative concentrations between pools with known amounts of standards may thus be obtained. While this example does not provide absolute concentrations for biomolecules, this example still has the advantages that parallel processing of samples is not required as with conventional SILAC and any sample source, not just cultured cells can be used to obtain data.

Following proteolysis, the lysate components are processed for MS. For example, they may be separated by chromatography and fed to MS. In this example, the concentration of the light-isotope isoform is determined by comparing the relative intensity to its heavy-isotope isoform. Because the amount of the heavy-isotope isoform is known in each of the pools, the relative concentrations of the light-isotope isoform may be determined. In these embodiments, to compare the expression proteins in a first cell pool and a second cell pool, two MS analyses must be performed versus one by conventional SILAC. However, each run will not require a control sample because the amount of added standard is known. Multiple MS analyses are within the capability of normal operations, for example, operations of a MS core lab.

Example 3

Further aspects of the present invention feature analyzing the relative abundance of multiple biomolecules, for example, proteins, simultaneously. In this example, there are for example several methods of generating multiple recombinantly expressed heavy-isotope labeled reference proteins.

For example, the practitioner may design multiple primers to multiple unrelated genes and amplify, subclone, and express these simultaneously. The final purified protein sample will contain a pool of multiple proteins in an unknown ratio. A quantitative amount of this pool may be spiked into the challenged cell lysates and the control cell lysate, and the relative abundance of proteins may be determined as discussed previously with respect to panel C of FIG. 2. In this example, only the relative abundance of each protein may be determined. However, the results of multiple experiments may be compared if a quantitative amount of the same reference protein pool was used.

In a second method, a practitioner may simply amplify, subclone, and express multiple genes in separate reactions. After quantifying the resulting proteins, the user may pool these in a known ratio. The user may then spike this pool into the challenged cell lysates and the control cell lysate, and the relative abundance of proteins may be determined as discussed previously with respect to panel C of FIG. 2. In this iteration, both the relative and absolute abundance of each protein may be determined.

In yet another method, the practitioner may design a single set of primers that target a DNA sequence region that is essentially identical amongst a family of genes. From a single PCR reaction of a cDNA library, a number of genes, gene fragments, isotypes, splice and/or sequence variants may be amplified. These products may then be subcloned, and expressed substantially simultaneously. The final purified protein sample will contain a pool of multiple proteins in an unknown ratio. A quantitative amount of this pool may be spiked into the challenged cell lysates and the control cell lysate, and the relative abundance of proteins may be determined as discussed previously with respect to panel C of FIG. 2. In this example, only the relative abundance of each protein may be determined. However, the results of multiple experiments may be compared if a quantitative amount of the same reference protein pool was used.

A variation of the above methods includes quantitation of one or more proteins or polypeptides in the pool. In this variation, both the relative and absolute abundance of each of the quantified proteins and polypeptides may be determined. Quantitation of each component of the reference standard pool may be determined. This may be accomplished by purification of each of the components followed by a quantitative assay using any of the common techniques known to those in the an or by any quantitation method available for the individual or class of protein or polypeptide.

Example 4

Figure 3:
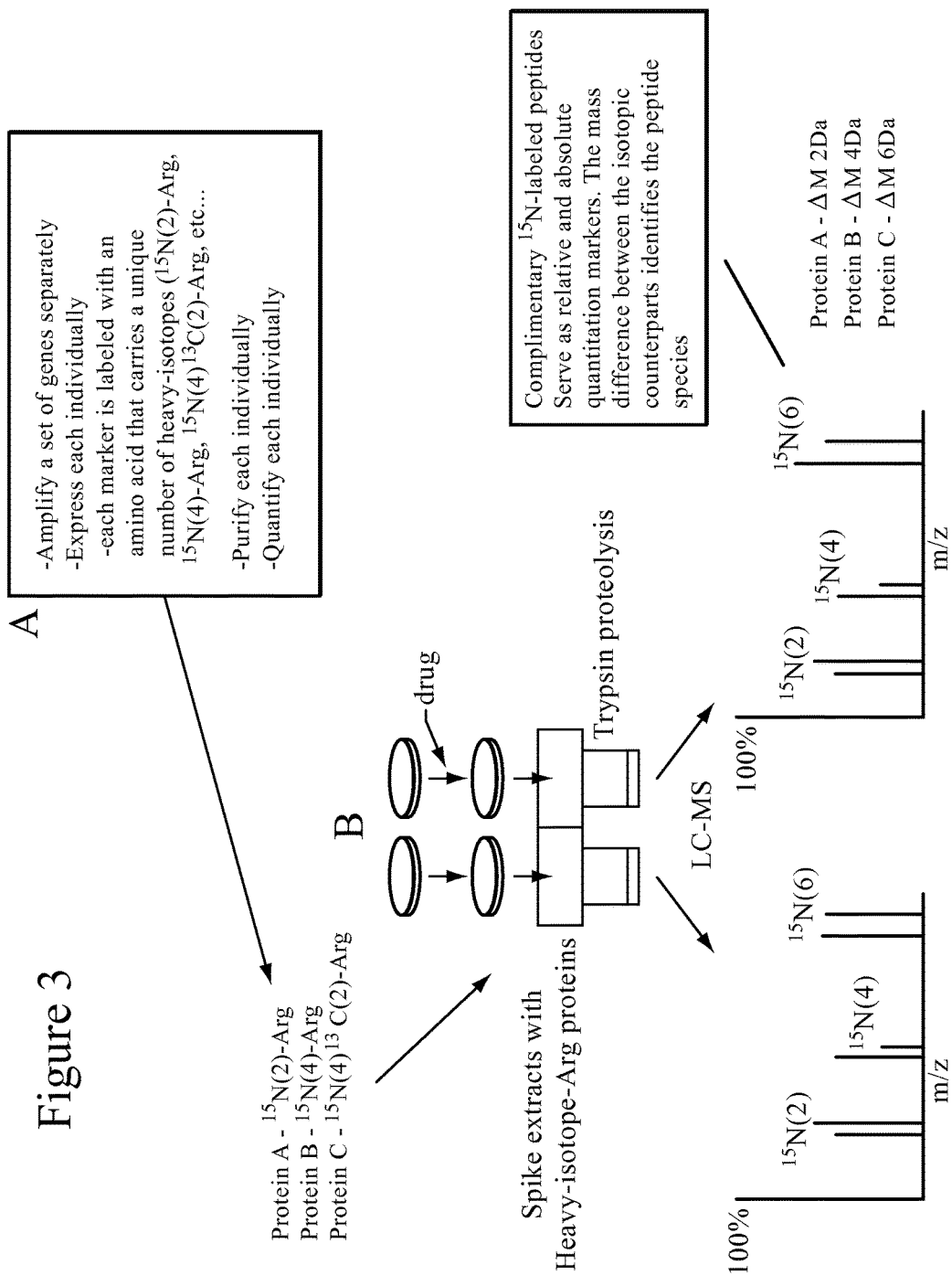
FIG. 3 schematically depicts certain embodiments of the present invention in which individual peptides that can be quantified are uniquely identified.

Another aspect of the present invention features quantifying biomolecules using unique multiple heavy-isotope labeled reference proteins. Multiple biomolecules can be differentially labeled so that fragments of different biomolecules can be individually identified. FIG. 3 illustrates this aspect of the invention. According to FIG. 3, a set of biomolecules, such as a set of proteins may be separately generated. For example, a set of genes may be selected and engineered into separate cells for differential expression. Each biomolecule may be labeled with an amino acid that contains a unique number of heavy-isotopes; for example, two, three, four or more proteins can be synthesized with different mass differences (e.g., one with heavy nitrogen, a second with hydrogen and carbon; a third with nitrogen, carbon, a heavy oxygen, etc.); thus a unique molecular mass, and unique mass shift from the naturally occurring light-isotope isoform.

FIG. 3A exemplifies three conditions with a unique isotope mix, an arginine with two $^{15}$N atoms, an arginine with four N atoms, and an arginine with four $^{15}$N and two $^{13}$C atoms. As would be apparent to those skilled in the art different residues might be used and different combinations of isotopes are possible in accordance with the present invention.

FIG. 3 shows three proteins, A, B and C with fragments that differ from native fragments by 2, 4 and 6 mass units, respectively. FIG. 3B exemplifies a drug treatment of samples before standard is added. After purification and optional quantification of each biomolecule, these biomolecules can be spiked in as standards.

Then MS, for example, MALDI, may be used to identify and compare or quantify amounts of each peptide and source protein from the samples. During MS analysis, the relative abundance between the heavy and light isotope isoforms can be measured. Further, the mass difference between the heavy and light isotope isoforms can be used to identify the specific protein in the mixture that produced that proteolytic fragment. In this example, no further sequencing information is needed to corroborate the identity of the mass ion.

Although this invention has been described in certain specific embodiments, many additional modifications and variations would be apparent to those skilled in the art. It is therefore to be understood that this invention may be practiced other than as specifically described. Thus, the present embodiments of the invention should be considered in all respects as illustrative and not restrictive.

What is claimed is:

1. A method of making an isotopically-labeled biomolecule standard comprising expressing a copy of a protein of interest in recombinant cells cultured in media that comprises at least one isotopically-labeled amino acid or amino acid residue, wherein the expressed copy of the protein incorporates the at least one isotopically-labeled amino acid or amino acid residue;

expressing a cognate protein of interest expressed in the recombinant cells cultured in media comprising at least one naturally-occurring cognate amino acid or amino acid residue in the absence of the at least one isotopically-labeled amino acid or amino acid residue, wherein the cognate protein of interest comprises the at least one naturally-occurring cognate amino acid or amino acid residue;

purifying the copy of the protein of interest, wherein the purified copy of the protein is not enzymatically or chemically digested, wherein the undigested, purified copy of the protein is used as an isotopically-labeled biomolecule standard; and quantitating the isotopically-labeled biomolecule standard by comparing the mass spectrometry peaks of pairs resulting from the isotopically-labeled biomolecule standard and the cognate protein of interest, wherein the mass of the isotopically-labeled biomolecule standard differs from the mass of the cognate protein of interest by an amount corresponding to the difference in mass between the isotopic label and the naturally-occurring cognate.

2. The method of claim 1, wherein the at least one isotoptically-labeled amino acid or amino acid residue comprises a non-radioactive isotope selected from the group consisting of $^{15}N$, $^{13}C$, $^{18}O$, $^{2}H$, $^{34}S$, and combinations thereof.

3. The method of claim 1, wherein the quantity being determined is a rely quantity.

4. The method of claim 1, wherein die quantity being determined is an absolute quantity.

5. The method of claim 1, wherein the cultured cells are prokaryotic cells.

6. The method of claim 5, wherein the prokaryotic cells are selected from the group consisting of *E. coli* cells, *Pseudomonas* cells, *Rhodobacter* cells, *Bacillus* cells, *Streptomyces* cells, *Erwinia* cells, *Klebsiella* cells, *Serratia* cells and *Salmonella* cells.

7. The method of claim 1, wherein the cells are eukaryotic cells.

8. The method of claim 1, wherein the cells are selected from the group consisting of yeast cells, mammalian cells, marsupial cells, avian cells, insect cells, fish cells, amphibian cells, reptile cells, and nematode cells.

9. The method of claim 1, wherein the copy is made using at least one amino acid with an isotope pool having a mass distribution different than that of naturally-occurring isotopes in the cognate protein of interest.

10. The method of claim 1, wherein the amino acid is selected the group consisting of Arg, Lys, Asp, Glu, Met, Trp, Ser, Thr, Tyr, and Asn.

* * * * *

UNITED STATES PATENT AND TRADEMARK OFFICE
CERTIFICATE OF CORRECTION

PATENT NO. : 10,753,905 B2
APPLICATION NO. : 15/597928
DATED : August 25, 2020
INVENTOR(S) : John F. Leite et al.

Page 1 of 1

It is certified that error appears in the above-identified patent and that said Letters Patent is hereby corrected as shown below:

On the Title Page

Item (60), delete "(60)" and insert --(62)--, therefor.

Signed and Sealed this
First Day of December, 2020

Andrei Iancu
*Director of the United States Patent and Trademark Office*